United States Patent [19]
Kiyooka

[11] Patent Number: 6,165,473
[45] Date of Patent: Dec. 26, 2000

[54] RICE CRACKERS INCLUDING FUNORI AND METHOD OF PRODUCING RICE CRACKERS INCLUDING FUNORI

[76] Inventor: Tomiko Kiyooka, 28-2 Hanaguri 1-Chome, Soka City, Saitama Pref, Japan

[21] Appl. No.: 09/328,974

[22] Filed: Jun. 9, 1999

[51] Int. Cl.$^7$ .............................. A61K 47/00; A61K 9/28; A61K 37/78; A23L 1/337; A23L 1/00

[52] U.S. Cl. ........................ 424/195.1; 424/439; 424/441; 426/615

[58] Field of Search ................................. 424/195.1, 439, 424/441, 615

[56] References Cited

U.S. PATENT DOCUMENTS 4,667,588   5/1987   Hayashi .

FOREIGN PATENT DOCUMENTS

| | | |
|---|---|---|
| 60-47666 | 3/1985 | Japan . |
| 60-47667 | 3/1985 | Japan . |
| 63-316732 | 12/1988 | Japan . |
| 2-289523 | 11/1990 | Japan . |
| 8-25895 | 3/1996 | Japan . |

OTHER PUBLICATIONS

Merriam Webster's Collegiate Dictionary, Tenth Edition. Merriam–Webster, Inc., Massachusetts. p. 659, 1993.

News Release Jun. 3, 1998—Red Seaweed–Derived Natural Oligosaccharides Discovered to Posess Cancer–Suppressing Properties.

*Primary Examiner*—Francisco Prats
*Assistant Examiner*—Susan D. Coe
*Attorney, Agent, or Firm*—Martin Fleit

[57] ABSTRACT

A rice cracker including Funori, which comprises not less than 50 wt % of rice powder, 1–20 wt % of Funori, and 1–20 wt % of sesame, and the method of producing said rice cracker, wherein said rice cracker contains a HIV-inhibiting element.

12 Claims, No Drawings

RICE CRACKERS INCLUDING FUNORI AND METHOD OF PRODUCING RICE CRACKERS INCLUDING FUNORI

BACKGROUND OF THE INVENTION

1. Field of the Invention

This invention relates to a new use of Funori, which is known to be one kind of red seaweed. In general, Funori is used to be mixed with wall soils or to form tablets of medicine. In addition, Funori is used as a combining material or as a washing agent of Japanese clothes from ancient times.

2. Description of Related Art

In the prior art, Funori is known to use a healthy food or to have cancer suppressing properties and anti-oxidant properties. However, Funori is not known to have HIV-inhibiting function.

The inventor have performed a long period of research and accumulated experiences, to show the fact that a Funori exhibits some particular anti-virus activity. AIDS (Acquired Immunodeficiency Syndrome) is a serious disease that leads the patients to death, therefore it is a remarkable problem of modern society. It is known that the disease is caused by the infection of HIV (Human Inmunodeficiency Virus), which is a retrovirus. The first step of the infection is adherence of this virus to human $T_4$ lymphocyte, succeeded by consecutive infection of other lymphocyte to disrupt immune system of its host.

That is, if the inhibition of the adherence of HIV to human lymphocyte or the inhibition of the activity of a substance essential for HIV proliferation could be achieved, it would give a novel mean for the inhibition of AIDS. Moreover, it would be also effective for other immune diseases, such as tetanus or collagen disease.

According to the knowledge described above, the aim of this invention is to provide a new method of using Funori, which enables the treatment of immune disease, based on the RBM (Biological Response Modifier) effect of Funori.

SUMMARY OF THE INVENTION

To attain said object, this invention provides a new method of producing a rice cracker including an effective element of Funori, which is effective for treating AIDS, by producing a rice cracker comprised by mixing a rice powder with Funori and baking it to rice cracker. Funori is included in the category of Red Seaweed, which is known in Japan by names such as Funori (*Gloiopeltis Furcata*) or Tengusa (Gelidum), derived mainly from seaweed of Gelidium or Gracilialis. The product derived from Funori is a gelatinous substance and consumed as a food with rich content of dietary fiber. Funori is also used as a glue for paper manufacturing. Moreover, Funori is effective for cancer suppression. However, it is not known that Funori is effective for the treatment of AIDS. This invention provides a new usage of Funori as an AIDS suppresser, based on its potential ability to improve immune function.

The present inventor invented a new method of using Funori. The inventor further studied for FUNORI to find that a rice cracker including Funori is effective for the suppression of AIDS. The inventor has knowledge that Funori has the inhibitory activity against tetanus and collagen disease. Therefore, the inventor assumed that, if Funori is used as a material of rice cracker with sufficient content, it would be effective for treatment of AIDS by improving the immune function.

The inventor has found the effectiveness of a rice cracker including Funori 1–20%, rice powder more than 50%, few water of less than 5–20% and 1–20% of sesame, by the experiments. The invention further provides a method of producing an AIDS busting rice cracker comprised by mixing rice powder of more than 50% with Funori of 1–20%, a few water of less than 20%, sesame of 1–20% and balling the mixture to the rice cracker.

The reason that the content of Funori is limited to about 1–20% is as follow. If the content of funori becomes over 20%, the rice cracker would be too soft to bake, and if the content of Funori becomes less than 1%, the obtained rice crackers would not be effective for suppressing AIDS. The preferable content of Funori in rice cracker would be 2–20%.

When said rice cracker including Funori and sesame is given to a person one sheet of 18 g per day, the blood glucose value have been remarkably reduced to the regular value of less than 120 from 180 after 30 days.

The food composition is as follows.

| Food | Raw Rice | Black sesame |
|---|---|---|
| Calorie | 344 | 1588 |
| Water | 145 | 7.1 |
| Albumen | 7.5 | 17.1 |
| Fat | 2.5 | 47.3 |
| Ash | 1.3 | 4.3 |
| Calcium (Ca) | 9 | 1,100 |
| Phosphorus (P) | 280 | 570 |
| Iron (Fe) | 1.0 | 16.3 |
| Hydrocarbon (C) | | |
| Starch | 73.4 | 19.1 |
| Fiber | 10.0 | 3.2 |
| Vitamin | | |
| A | 0 | 35 |
| $B_1$ | 0.4 | 0.5 |
| $B_2$ | 0.1 | 0.1 |
| C | 0 | 0 |

Funori of 1–20 wt % was mixed with said food composition including rice powder of less than 50 wt % and sesame of 1–20 wt % and water less than 20 wt % and kneaded and baked into dry rice cracker of 3510 sheets. When one sheet of said rice cracker of 18 g per day was given to a person who is holding HIV, the blood glucose value after eating of Funori including rice cracker for 30 days was remarkably reduced to less than 120 from 180. The rice cracker including Funori and sesame is quiet effective to diabetes mellitus. As shown in DATA OF MEASURING HIV ACTIVITY-1~8 and their Resume.

The anti-HIV activity is measured as following method.

Method of measurement: MTT (tetrazolium) method

Infection target cell: MT-4 cell

Virus: HTLV-IIIB (infection value: $2.0 \times 10^6$ PFU/ml)

The summary of anti-virus activity measurement: Various densities of test substances are mixed with the MT-4 cell ($2.5 \times 10^4$/well, Mol: 0.01) on a micro-titerplate with 96 wells, just after infection of the cells.

EMBODIMENT 1

| | |
|---|---|
| Rice flour | 60 kg |
| Sesame | 25 kg |
| Funori | 5.5 kg |
| Water | 9.5 kg |
| Total | 100 kg |

The Funori is fused and mixed with rice flour and sesame with few water and the obtained gelatinous substances are kneaded into raw rice crackers of 3510 sheets and drying for 13 hours in 40° C., baked by using 24 electric bulb of 300 W for about 5–6 minutes, rice crackers of 3510 sheets is obtained in which one sheet is about 18 g.

Thus obtained Funori including rice cracker was taken one sheet which is about 18g per day for about 30 days by HIV holding person. After 30 days, HIV holding person have recovered from AIDS after taking said funori including rice cracker. This fact is checked by taking his blood test.

The content of Funori in rice cracker is 1–20 wt %, the content of Funori of less than 1% is not effective for treating AIDS. The content of Funori in rice cracker is more than 20 wt %, the rice cracker become so soft and it can not obtained hard rice cracker.

EMBODIMENT 2

| | |
|---|---|
| Rice flour | 60 kg |
| Sesame | 20 kg |
| Funori | 5 kg |
| Water | 20 kg |
| Total | 105 kg |

The materials are mixed and the obtained gelatinous substances are kneaded into raw rice crackers of 3510 sheets. Raw rice crackers of 3510 sheets have dried for 13 hours on 40° C. and baked by rotating and heating by 24 electric bulbs of 300 W and baking during repeating of several time of up-setting for baking for 5~6 minutes.

Another EMBODIMENTS are applied by Test density of 2.0%, 1.0%, 0.5%, 0.25%, 0.125%, 0.0625%, 0.0313% and 0.015%, 0.0078%, 0%. As shown in DATA OF MEASURING HIV ACTIVITY-1, Test density of 2.0~0.0313% of Funori in rice cracker is recognized as effectiveness of more than 13.04~127.69%.

As shown in DATA OF MEASURING HIV ACTIVITY-2, Test density of Funori in rice cracker of 1000, 200, 40, 8, 1.6, 0.32, 0.0640 and 0.0128 ($\mu$g/ml) is recognized effectiveness of more than 8.11 to 182.95(%).

As shown in DATA OF MEASURING HIV ACTIVITY-3, Test densities of Funori in rice cracker of 1000~0.3200 ($\mu$g/ml) are recognized Effectiveness 90.05~172.85(%).

As shown in DATA OF MEASURING HIV ACTIVITY-4, Test densities of Funori in rice cracker of 2.0~0.0156(%) is recognized as Effectiveness of 20.79~100.36(%).

As shown in DATA OF MEASURING HIV ACTIVITY-5, Test densities of Funori in rice cracker of 0.0128~1000 ($\mu$g/ml) are recognized as Effectiveness of 13.15~142.04 (%).

As shown in DATA OF MEASURING HIV ACTIVITY-6, Test densities of Funori of 20~0.0013 ($\mu$M) in rice cracker are recognized as Effectiveness of 36.55~84.24%.

As shown in DATA OF MEASURING HIV ACTIVITY-7, Test densities of Funori ($\mu$g/ml) of 1000 to 0.32 are recognized as Effectiveness of 107.53~162.55%.

As shown in DATA OF MEASURING HIV ACTIVITY-8, Test densities of 20 to 0.0013 ($\mu$M) are recognized as Effectiveness of 54.83~90.73%.

EMBODIMENT 3

| | |
|---|---|
| Rice flour | 50 kg |
| Sesame | 20 kg |
| Funori | 3 kg |
| Water | 7 kg |
| Total | 80 kg |

Funori is fused on 40° C. and mixed with rice flour, sesame and few water, are kneaded making raw rice cracker of 3510 sheet and drying on 40° C. for 13 hours, and baking by rotating and turning upset on heating by lighting 24 lamps of 300 W, rice flour and sesame of test substance DS-9 as shown in DATA OF MEASURING HIV ACTIVITY-5.

The same test is also applied to Non infection MT-4 cell as comparative. Test density of Funori of 20.0~0.0001~0% is added to rice powder and sesame, kneaded applied for forming, drying and baked for making funori including rice cracker.

DATA of Measuring HIV ACTIVITY-4 shows Test density of 2.0%~0.0078%~0% of Test substance Funori-2. Test substance is FULNORI-2 and HIV infection MT-4 cell (HIV strain; HTLV-IIIB) is used together with Non infection MT-4 cell (comparison) as shown in DATA of Measuring HIV ACTIVITY-4.

Test density of Funori of 1000~0.0026~0 ($\mu$g/ml) is added with said rice powder and sesame and obtained DATA of MEASURING HIV ACTIVITY-5. Test density of Funori of 20.0~0.0001~0% is added with said rice powder and sesame kneaded, formed, dried and baked for making funori including rice cracker as shown in DATA of MEASURING HIV ACTIVITY-6 as same manner of EMBODIMENT 1.

Test density of Funori of 1000~0.0026~0 ($\mu$g/ml) is added with said rice flour, sesame and few water, kneaded, formed, dried, and baked for making funori including rice cracker as shown in DATA OF MEASURING HIV ACTIVITY-7. Test density of Funori of 20~0.0001~0 ($\mu$M) is added with said rice flour, sesame and few water, kneaded, formed, dried and baked for making funori including rice cracker as shown in DATA OF MEASURING ACTIVITY-8.

As shown in Embodiments 1 and 3, it is found the fact that the rice cracker including Funori and sesame is quite effective for suppressing HIV activity, and also effective for tetanus, collagen disease and immune deficiency.

It is also found that the rice cracker is free from harmful side-effects, so that it is entirely harmless to take said rice cracker.

Report of Test Result for Detecting Anti-HIV Activity

Test substance: Funori 1
Method for Test: MTT (Tetrazolium) method
test substance of cell: MT-4 cell
virus: HTLV-IIIB (infection value: 2.0×10, PFU/ml)
abstract of test method:
HIV infected MT-4 cell ($2.5 \times 10^4$/well, Mol: 0.01) is given with several content of test sample substance just after infected in micro titerplate of 96 holes. For detecting a cytotoxicity (i.e. poisonous property) of test substance to MT-4 cell, several density of non-virus infected cells are also cultivated with said test substance in the same manner. Said all materials are cultivated at 37° C. for 5 days in a $CO_2$-incubator, thereafter the number of cells alive is measured by the MTT (Tetrazolium) method.

Anti-virus activity of the test sample is indicated by 50% protection density ($EC_{50}$: 50% effective concentration) for inhibiting 50% of cytotoxicity inducted by HIV infection and cytotoxycity of test substance is indicated by 50% cell lesin concentrations ($CC_{50}$: 50% cytotoxic concentration). Selectivity Index (SI) is calculated as $CC_5/ED_{50}$ (ref: Pauwels et al., J Virol Methods, 20 (1988) p309–321).

Data of Measuring HIV Activity is measured by a different test density of Funori of 2.0%, 1%, 0.5%, 0.25%, 0.125%, 0.0625%, 0.0313%, 0.0156%, 0.0078% and 0% as shown in DATA OF MEASURING HIV ACTIVITY-1.

DATA OF MEASURING HIV ACTIVITY-1

Tested substance: FUNORI-1

HIV infection MT-4 cell (HIV strain: HTLV-IIIB)

|  | Measurement value (OD) | | | | |
|---|---|---|---|---|---|
| Test density (%) | Background | Medium value | Mean value | Standard deviation | Effectiveness (%) |
| 2.0000 | 0.005 | 0.659 | 0.598 | 0.103 | 127.69 |
| 1.0000 | 0.004 | 0.678 | 0.713 | 0.066 | 132.27 |
| 0.5000 | 0.030 | 0.683 | 0.680 | 0.020 | 127.46 |
| 0.2500 | 0.002 | 0.487 | 0.526 | 0.059 | 89.02 |
| 0.1250 | 0.002 | 0.491 | 0.475 | 0.044 | 89.93 |
| 0.0625 | 0.001 | 0.186 | 0.206 | 0.028 | 20.37 |
| 0.0313 | 0.001 | 0.154 | 0.155 | 0.015 | 13.04 |
| 0.0156 | 0.000 | 0.095 | 0.106 | 0.023 | −0.23 |
| 0.0078 | 0.001 | 0.089 | 0.089 | 0.001 | −1.83 |
| 0 | 0.001 | 0.097 | 0.091 | 0.010 | 0.00 |

Non infection MT-4 cell

|  | Measured value (OD) | | | | | Virulenced |
|---|---|---|---|---|---|---|
| Test density (%) | Background | Medium value | Mean value | Standard deviation | Alived cell (%) | cell (%) |
| 2.0000 | 0.017 | 0.795 | 0.760 | 0.063 | 145.97 | −45.97 |
| 1.0000 | 0.013 | 0.749 | 0.748 | 0.010 | 138.09 | −38.09 |
| 0.5000 | 0.031 | 0.719 | 0.721 | 0.003 | 129.08 | −29.08 |
| 0.2500 | 0.012 | 0.586 | 0.610 | 0.036 | 107.69 | −7.69 |
| 0.1250 | 0.012 | 0.677 | 0.674 | 0.006 | 124.77 | −24.77 |
| 0.0625 | 0.010 | 0.567 | 0.575 | 0.059 | 104.50 | −4.50 |
| 0.0313 | 0.010 | 0.613 | 0.604 | 0.016 | 113.13 | −13.13 |
| 0.0156 | 0.010 | 0.582 | 0.563 | 0.034 | 107.32 | −7.32 |
| 0.0078 | 0.011 | 0.565 | 0.568 | 0.007 | 103.94 | −3.94 |
| 0 | 0.009 | 0.542 | 0.548 | 0.013 | 100.00 | 0.00 |
| 50% effective density (EC50) | | | | 0.0840% | | |
| 90% effective density (EC90) | | | | 0.2545% | | |
| 50% cell virulence density (CC50) | | | | error % | | |
| Effective coefficient (SI = CC50/EC50) | | | | error | | |

Comment: said DATA 1 is shown in FIG. 1.

DATA OF MEASURING HIV ACTIVITY-2

Tested substance: DS-8

HIV infection MT-4 cell (HIV strain: HTLV-IIIB)

|  | Measurement value (OD) | | | | |
|---|---|---|---|---|---|
| Test density (ug/ml)) | Background | Medium value | Mean value | Standard deviation | Effectiveness (%) |
| 1000.0000 | 0.003 | 0.970 | 0.986 | 0.041 | 182.95 |
| 200.0000 | 0.028 | 0.689 | 0.674 | 0.045 | 119.33 |
| 40.0000 | 0.001 | 0.624 | 0.599 | 0.072 | 111.43 |
| 8.0000 | 0.001 | 0.618 | 0.610 | 0.030 | 110.19 |
| 1.6000 | 0.001 | 0.484 | 0.502 | 0.064 | 82.33 |
| 0.3200 | 0.002 | 0.179 | 0.180 | 0.022 | 18.71 |
| 0.0640 | 0.002 | 0.129 | 0.129 | 0.016 | 8.32 |
| 0.0128 | 0.002 | 0.128 | 0.123 | 0.011 | 8.11 |
| 0.0026 | 0.002 | 0.083 | 0.087 | 0.011 | −1.25 |
| 0 | 0.001 | 0.083 | 0.087 | 0.005 | 0.00 |

Non infection MT-4 cell

|  | Measured value (OD) | | | | Alived cell | Virulenced cell |
| --- | --- | --- | --- | --- | --- | --- |
| Test density (ug/ml) | Background | Medium value | Mean value | Standard deviation | (%) | (%) |
| 1000.0000 | 0.011 | 0.980 | 0.964 | 0.036 | 170.47 | −70.47 |
| 200.0000 | 0.027 | 0.554 | 0.587 | 0.048 | 92.79 | 7.21 |
| 40.0000 | 0.008 | 0.583 | 0.592 | 0.021 | 101.23 | −1.23 |
| 8.0000 | 0.008 | 0.551 | 0.546 | 0.062 | 95.61 | 4.39 |
| 1.6000 | 0.008 | 0.505 | 0.512 | 0.028 | 87.52 | 12.48 |
| 0.3200 | 0.007 | 0.565 | 0.529 | 0.061 | 98.24 | 1.76 |
| 0.0640 | 0.009 | 0.566 | 0.569 | 0.010 | 98.07 | 1.93 |
| 0.0128 | 0.009 | 0.580 | 0.576 | 0.008 | 100.53 | −0.53 |
| 0.0026 | 0.008 | 0.585 | 0.549 | 0.059 | 101.58 | −1.58 |
| 0 | 0.008 | 0.576 | 0.541 | 0.062 | 100.00 | 0.00 |

50% effective density (EC50)    0.7062 ug/ml
90% effective density (EC90)    2.4920 ug/ml
50% cell virulence density (CC50)    error ug/ml
Effective coefficient (SI = CC50/EC50)    error Comment: said DATA 2 is shown in FIG. 2

DATA OF MEASURING HIV ACTIVITY-3

Tested substance: CRDS-8
HIV infection MT-4 cell (HIV strain: HTLV-IIIB)

|  | Measurement value (OD) | | | | Effectiveness |
| --- | --- | --- | --- | --- | --- |
| Test density (ug/ml)) | Back-ground | Medium value | Mean value | Standard deviation | (%) |
| 1000.0000 | 0.003 | 0.846 | 0.732 | 0.172 | 172.85 |
| 200.0000 | 0.000 | 0.520 | 0.528 | 0.026 | 99.77 |
| 40.0000 | 0.000 | 0.544 | 0.540 | 0.018 | 105.20 |
| 8.0000 | 0.001 | 0.504 | 0.529 | 0.037 | 95.93 |
| 1.6000 | 0.002 | 0.531 | 0.517 | 0.022 | 101.81 |
| 0.3200 | 0.002 | 0.479 | 0.485 | 0.046 | 90.05 |
| 0.0640 | 0.003 | 0.097 | 0.097 | 0.002 | 3.39 |
| 0.0128 | 0.003 | 0.083 | 0.085 | 0.006 | 0.23 |
| 0.0026 | 0.003 | 0.082 | 0.083 | 0.003 | 0.00 |
| 0 | 0.003 | 0.082 | 0.081 | 0.003 | 0.00 |

Non infection MT-4 cell

|  | Measured value (OD) | | | | Alived cell | Virulenced cell |
| --- | --- | --- | --- | --- | --- | --- |
| Test density (ug/ml) | Background | Medium value | Mean value | Standard deviation | (%) | (%) |
| 1000.0000 | 0.013 | 0.701 | 0.644 | 0.200 | 131.87 | −31.87 |
| 200.0000 | 0.011 | 0.522 | 0.513 | 0.025 | 98.09 | 1.91 |
| 40.0000 | 0.010 | 0.530 | 0.518 | 0.016 | 99.81 | 0.19 |
| 8.0000 | 0.009 | 0.494 | 0.489 | 0.017 | 93.13 | 6.87 |
| 1.6000 | 0.008 | 0.497 | 0.500 | 0.017 | 93.89 | 6.11 |
| 0.3200 | 0.008 | 0.518 | 0.520 | 0.018 | 97.90 | 2.10 |
| 0.0640 | 0.008 | 0.502 | 0.505 | 0.007 | 94.85 | 5.15 |
| 0.0128 | 0.007 | 0.520 | 0.505 | 0.021 | 98.47 | 1.53 |
| 0.0026 | 0.007 | 0.504 | 0.503 | 0.009 | 95.42 | 4.58 |
| 0 | 0.008 | 0.529 | 0.525 | 0.011 | 100.00 | 0.00 |

50% effective density (EC50)    0.1521 ug/ml
90% effective density (EC90)    0.3197 ug/ml
50% cell virulence density (CC50)    error ug/ml
Effective coefficient (SI = CC50/EC50)    error Comment: said DATA 3 is shown in FIG. 3

DATA OF MEASURING HIV ACTIVITY-4

Tested substance: FUNORI-2
HIV infection MT-4 cell (HIV strain: HTLV-IIIB)

|  | Measurement value (OD) | | | | Effectiveness |
| --- | --- | --- | --- | --- | --- |
| Test density (%) | Background | Medium value | Mean value | Standard deviation | (%) |
| 2.0000 | 0.026 | 0.699 | 0.699 | 0.001 | 100.36 |
| 1.0000 | 0.027 | 0.735 | 0.725 | 0.015 | 106.63 |
| 0.5000 | 0.026 | 0.745 | 0.739 | 0.009 | 108.60 |
| 0.2500 | 0.027 | 0.756 | 0.758 | 0.012 | 110.39 |
| 0.1250 | 0.026 | 0.766 | 0.764 | 0.011 | 112.37 |
| 0.0625 | 0.025 | 0.679 | 0.684 | 0.049 | 96.95 |
| 0.0313 | 0.025 | 0.480 | 0.496 | 0.059 | 61.29 |
| 0.0156 | 0.024 | 0.253 | 0.292 | 0.055 | 20.79 |
| 0.0078 | 0.024 | 0.185 | 0.205 | 0.029 | 8.60 |
| 0 | 0.023 | 0.136 | 0.138 | 0.007 | 0.00 |

Non infection MT-4 cell

|             | Measured value (OD) | | | | Alived cell | Virulenced cell |
| Test density (%) | Background | Medium value | Mean value | Standard deviation | (%) | (%) |
| --- | --- | --- | --- | --- | --- | --- |
| 2.0000 | 0.027 | 0.702 | 0.699 | 0.007 | 100.60 | −0.60 |
| 1.0000 | 0.026 | 0.714 | 0.712 | 0.005 | 102.53 | −2.53 |
| 0.5000 | 0.026 | 0.740 | 0.743 | 0.016 | 106.40 | −6.40 |
| 0.2500 | 0.027 | 0.752 | 0.746 | 0.009 | 108.04 | −8.04 |
| 0.1250 | 0.027 | 0.769 | 0.764 | 0.009 | 110.57 | −10.57 |
| 0.0625 | 0.026 | 0.755 | 0.755 | 0.004 | 108.63 | −8.63 |
| 0.0313 | 0.025 | 0.743 | 0.742 | 0.004 | 106.99 | −6.99 |
| 0.0156 | 0.025 | 0.719 | 0.726 | 0.015 | 103.42 | −3.42 |
| 0.0078 | 0.025 | 0.741 | 0.733 | 0.012 | 106.70 | −6.70 |
| 0 | 0.025 | 0.696 | 0.697 | 0.007 | 100.00 | 0.00 |

| | |
| --- | --- |
| 50% effective density (EC50) | 0.0258% |
| 90% effective density (EC90) | 0.0546% |
| 50% cell virulence density (CC50) | error % |
| Effective coefficient (SI = CC50/EC50) | error |

Comment: said DATA 4 is shown in FIG. 4.

DATA OF MEASURING HIV ACTIVITY-5

Tested substance: DS-9
HIV infection MT-4 cell (HIV strain: HTLV-IIIB)

|                     | Measurement value (OD) | | | | Effectiveness |
| Test density (ug/ml) | Back-ground | Medium value | Mean value | Standard deviation | (%) |
| --- | --- | --- | --- | --- | --- |
| 1000.0000 | 0.029 | 0.418 | 0.550 | 0.190 | 51.48 |
| 200.0000 | 0.030 | 0.908 | 0.835 | 0.124 | 142.04 |
| 40.0000 | 0.027 | 0.777 | 0.802 | 0.039 | 118.33 |
| 8.0000 | 0.025 | 0.741 | 0.755 | 0.025 | 112.04 |
| 1.6000 | 0.025 | 0.662 | 0.681 | 0.042 | 97.41 |
| 0.3200 | 0.026 | 0.352 | 0.391 | 0.067 | 39.81 |
| 0.0640 | 0.025 | 0.358 | 0.351 | 0.036 | 41.11 |
| 0.0128 | 0.024 | 0.206 | 0.200 | 0.032 | 13.15 |
| 0.0026 | 0.024 | 0.144 | 0.148 | 0.005 | 1.67 |
| 0 | 0.024 | 0.135 | 0.137 | 0.008 | 0.00 |

Non infection MT-4 cell

|             | Measured value (OD) | | | | Alived cell | Virulenced cell |
| Test density (ug/ml) | Background | Medium value | Mean value | Standard deviation | (%) | (%) |
| --- | --- | --- | --- | --- | --- | --- |
| 1000.0000 | 0.028 | 0.669 | 0.682 | 0.096 | 98.46 | 1.54 |
| 200.0000 | 0.027 | 0.836 | 0.835 | 0.003 | 124.35 | −24.35 |
| 40.0000 | 0.025 | 0.812 | 0.806 | 0.011 | 120.96 | −20.96 |
| 8.0000 | 0.024 | 0.768 | 0.769 | 0.009 | 114.33 | −14.33 |
| 1.6000 | 0.024 | 0.684 | 0.685 | 0.012 | 101.39 | −1.39 |
| 0.3200 | 0.023 | 0.669 | 0.665 | 0.032 | 99.23 | 0.77 |
| 0.0640 | 0.024 | 0.685 | 0.683 | 0.010 | 101.54 | −1.54 |
| 0.0128 | 0.023 | 0.685 | 0.676 | 0.020 | 101.69 | −1.69 |
| 0.0026 | 0.024 | 0.680 | 0.678 | 0.011 | 100.77 | −0.77 |
| 0 | 0.023 | 0.674 | 0.674 | 0.007 | 100.00 | 0.00 |

| | |
| --- | --- |
| 50% effective density (EC50) | 0.5052 ug/ml |
| 90% effective density (EC90) | 1.3008 ug/ml |
| 50% cell virulence density (CC50) | error ug/ml |
| Effective coefficient (SI = CC50/EC50) | error |

Comment: said DATA 5 is shown in FIG. 5

DATA OF MEASURING HIV ACTIVITY-6

Tested substance: AZT-8
HIV infection MT-4 cell (HIV strain: HTLV-IIIB)

| Test density (uM)) | Measurement value (OD) | | | | Effectiveness (%) |
| | Background | Medium value | Mean value | Standard deviation | |
| --- | --- | --- | --- | --- | --- |
| 20.0000 | 0.002 | 0.222 | 0.220 | 0.009 | 29.82 |
| 4.0000 | 0.001 | 0.453 | 0.449 | 0.008 | 81.84 |
| 0.8000 | 0.025 | 0.490 | 0.482 | 0.015 | 84.75 |
| 0.1600 | 0.000 | 0.485 | 0.487 | 0.014 | 89.24 |
| 0.0320 | 0.002 | 0.383 | 0.407 | 0.039 | 65.92 |
| 0.0064 | 0.002 | 0.373 | 0.390 | 0.056 | 3.68 |
| 0.0013 | 0.003 | 0.253 | 0.264 | 0.018 | 36.55 |
| 0.0003 | 0.003 | 0.111 | 0.111 | 0.009 | 4.71 |
| 0.0001 | 0.003 | 0.080 | 0.081 | 0.005 | −2.24 |
| 0 | 0.003 | 0.090 | 0.088 | 0.007 | 0.00 |

Non infection MT-4 cell

| Test density (ug/ml) | Measured value (OD) | | | | Alived cell (%) | Virulenced cell (%) |
|---|---|---|---|---|---|---|
| | Background | Medium value | Mean value | Standard deviation | | |
| 500.0000 | 0.009 | 0.026 | 0.026 | 0.004 | 3.55 | 96.45 |
| 100.0000 | 0.009 | 0.030 | 0.028 | 0.004 | 4.30 | 95.70 |
| 20.0000 | 0.027 | 0.207 | 0.199 | 0.019 | 34.02 | 65.98 |
| 4.0000 | 0.010 | 0.453 | 0.453 | 0.006 | 83.18 | 16.82 |
| 0.8000 | 0.008 | 0.398 | 0.418 | 0.037 | 73.27 | 26.73 |
| 0.1600 | 0.008 | 0.437 | 0.440 | 0.018 | 80.56 | 19.44 |
| 0.0320 | 0.008 | 0.500 | 0.475 | 0.038 | 92.34 | 7.66 |
| 0.0064 | 0.009 | 0.517 | 0.494 | 0.041 | 95.33 | 4.67 |
| 0.0013 | 0.008 | 0.480 | 0.470 | 0.038 | 88.60 | 11.40 |
| 0 | 0.009 | 0.542 | 0.503 | 0.063 | 100.00 | 0.00 |

50% effective density (EC50)  0.0028 uM
90% effective density (EC90)  error uM
50% cell virulence density (CC50)  11.8528 uM
Effective coefficient (SI = CC50/EC50)  4170

Comment: said DATA 6 is shown in FIG. 6

DATA OF MEASURING HIV ACTIVITY-7

Tested substance: CRDS-9
HIV infection MT-4 cell (HIV strain: HTLV-IIIB)

| Test density (ug/ml)) | Measurement value (OD) | | | | Effectiveness (%) |
|---|---|---|---|---|---|
| | Background | Medium value | Mean value | Standard deviation | |
| 1000.0000 | 0.026 | 0.977 | 0.991 | 0.021 | 162.55 |
| 200.0000 | 0.026 | 0.815 | 0.804 | 0.031 | 131.27 |
| 40.0000 | 0.024 | 0.733 | 0.731 | 0.021 | 115.83 |
| 8.0000 | 0.024 | 0.717 | 0.711 | 0.008 | 112.74 |
| 1.6000 | 0.023 | 0.690 | 0.682 | 0.016 | 107.72 |
| 0.3200 | 0.023 | 0.689 | 0.687 | 0.005 | 107.53 |
| 0.0640 | 0.023 | 0.177 | 0.277 | 0.156 | 8.69 |
| 0.0128 | 0.023 | 0.147 | 0.159 | 0.025 | 2.90 |
| 0.0026 | 0.023 | 0.152 | 0.153 | 0.003 | 3.86 |
| 0 | 0.023 | 0.132 | 0.131 | 0.003 | 0.00 |

Non infection MT-4 cell

| Test density (ug/ml) | Measured value (OD) | | | | Alived cell (%) | Virulenced cell (%) |
|---|---|---|---|---|---|---|
| | Background | Medium value | Mean value | Standard deviation | | |
| 1000.0000 | 0.026 | 0.950 | 0.955 | 0.008 | 147.37 | −47.37 |
| 200.0000 | 0.024 | 0.757 | 0.773 | 0.027 | 116.91 | −16.91 |
| 40.0000 | 0.023 | 0.696 | 0.698 | 0.014 | 107.34 | −7.34 |
| 8.0000 | 0.023 | 0.695 | 0.679 | 0.025 | 107.18 | −7.18 |
| 1.6000 | 0.023 | 0.660 | 0.657 | 0.010 | 101.59 | −1.59 |
| 0.3200 | 0.022 | 0.681 | 0.669 | 0.020 | 105.10 | −5.10 |
| 0.0640 | 0.023 | 0.665 | 0.665 | 0.016 | 102.39 | −2.39 |
| 0.0128 | 0.024 | 0.689 | 0.688 | 0.015 | 106.06 | −6.06 |
| 0.0026 | 0.024 | 0.688 | 0.676 | 0.018 | 105.90 | −5.90 |
| 0 | 0.023 | 0.650 | 0.638 | 0.034 | 100.00 | 0.00 |

50% effective density (EC50)  0.1254 ug/ml
90% effective density (EC90)  0.2405 ug/ml
50% cell virulence density (CC50)  error ug/ml
Effective coefficient (SI = CC50/EC50)  error Comment: said DATA 7 is shown in FIG. 7

DATA OF MEASURING HIV ACTIVITY-8

Tested substance: AZT-9
HIV infection MT-4 cell (HIV strain: HTLV-IIIB)

| Test density (uM) | Measurement value (OD) | | | | Effectiveness (%) |
|---|---|---|---|---|---|
| | Background | Medium value | Mean value | Standard deviation | |
| 20.0000 | 0.025 | 0.328 | 0.310 | 0.037 | 32.05 |
| 4.0000 | 0.026 | 0.572 | 0.584 | 0.023 | 78.96 |
| 0.8000 | 0.026 | 0.622 | 0.622 | 0.013 | 88.61 |
| 0.1600 | 0.025 | 0.613 | 0.618 | 0.026 | 87.07 |
| 0.0320 | 0.025 | 0.622 | 0.632 | 0.024 | 88.80 |
| 0.0064 | 0.025 | 0.632 | 0.644 | 0.025 | 90.73 |
| 0.0013 | 0.023 | 0.444 | 0.448 | 0.009 | 54.83 |
| 0.0003 | 0.023 | 0.210 | 0.210 | 0.018 | 9.65 |
| 0.0001 | 0.023 | 0.150 | 0.163 | 0.027 | −1.93 |
| 0 | 0.023 | 0.160 | 0.160 | 0.006 | 0.00 |

Non infection MT-4 cell

| Test density (ug/ml) | Measured value (OD) | | | | Alived cell (%) | Virulenced cell (%) |
|---|---|---|---|---|---|---|
| | Background | Medium value | Mean value | Standard deviation | | |
| 500.0000 | 0.024 | 0.052 | 0.052 | 0.002 | 3.83 | 96.17 |
| 100.0000 | 0.025 | 0.054 | 0.056 | 0.004 | 3.99 | 96.01 |
| 20.0000 | 0.024 | 0.190 | 0.198 | 0.015 | 25.00 | 75.00 |
| 4.0000 | 0.025 | 0.581 | 0.582 | 0.013 | 84.82 | 15.18 |
| 0.8000 | 0.025 | 0.606 | 0.605 | 0.006 | 88.65 | 11.35 |
| 0.1600 | 0.025 | 0.599 | 0.601 | 0.003 | 87.58 | 12.42 |
| 0.0320 | 0.025 | 0.648 | 0.646 | 0.012 | 95.09 | 4.91 |
| 0.0064 | 0.025 | 0.660 | 0.654 | 0.011 | 96.93 | 3.07 |
| 0.0013 | 0.025 | 0.662 | 0.669 | 0.018 | 97.24 | 2.76 |
| 0 | 0.025 | 0.680 | 0.679 | 0.008 | 100.00 | 0.00 |

| | |
|---|---|
| 50% effective density (EC50) | 0.0011 uM |
| 90% effective density (EC90) | 0.0062 uM |
| 50% cell virulence density (CC50) | 10.2074 uM |
| Effective coefficient (SI = CC50/EC50) | 9326 |

Comment: said DATA 8 is shown in FIG. 8

Resume

Test 1

| Test agent | CC50 ($\mu$g/ml) | EC50 ($\mu$g/ml) | SI |
|---|---|---|---|
| Funori-1 (%) | >10.00 | =0.084 | >119 |
| Dexstran sulfate | >1000.00 | =0.706 | >1416 |
| Curdlan sulfate | >1000.00 | =0.15 | >6667 |
| AZT ($\mu$M) | =11.85 | =0.0028 | =4170 |

Test 2

| Test agent | CC50 ($\mu$g/ml) | EC50 ($\mu$g/ml) | SI |
|---|---|---|---|
| Funori-2 (%) | >10.00 | =0.0258 | >388 |
| Dexstran sulfate | >1000.00 | =0.505 | >1980 |
| Curdlan sulfate | >1000.00 | =0.125 | >8000 |
| AZT ($\mu$M) | =10.21 | =0.0011 | =9326 |

What is claimed is:

1. A rice cracker consisting essentially of at least 50 wt % of rice, 1 to 20 wt % of funori, and 1 to 20 wt % of sesame.

2. A rice cracker according to claim 1 wherein the funori is present from about 3 wt % to about 7.5 wt %.

3. A rice cracker according to claim 1 where the funori is present from about 4 wt % to about 6 wt %.

4. A rice cracker according to claim 1 wherein the weight of the cracker is about 18 grams and the funori content is less than about 3.5 grams.

5. A rice cracker according to claim 4 wherein the funori content is less than 1 gram.

6. A rice cracker consisting essentially of rice, sesame and funori wherein the funori content is from about 0.35 grams to about 3.5 grams.

7. A rice cracker according to claim 6 wherein the funori content is less than about 1 gram.

8. A method of producing a rice cracker including Funori, the method comprising the steps of:

mixing more than 50 wt % of rice powder with 1–20 wt % of Funori, 1–20% of sesame, not more than 20 wt % of water, kneading and forming and drying the mixture to prepare a raw rice cracker sheet and baking said raw rice cracker sheet.

9. A method of producing a rice cracker including Funori as defined in claim 8, wherein thus obtained rice cracker has HIV inhibiting function.

10. A method of producing a rice cracker including Funori as defined in claim 8, wherein thus obtained rice cracker contains a HIV inhibiting element.

11. A method of treating a person infected with HIV comprising orally introducing into said person an effective amount of Funori in the form of a rice cracker.

12. The method of claim 11 wherein the rice cracker contains no less than 50 wt % of rice powder, 1–20 wt % of Funori and 1–20 wt % of sesame.

* * * * *